(12) United States Patent
Jager Lezer et al.

(10) Patent No.: US 7,993,632 B2
(45) Date of Patent: Aug. 9, 2011

(54) COMPOSITION FOR COATING KERATIN FIBRES HAVING A THREADING NATURE

(75) Inventors: Nathalie Jager Lezer, Verrieres-le-Buisson (FR); Valérie de la Poterie, le Chatelet en Brie (FR)

(73) Assignee: L'Oreal S.A., Paris (FR)

( * ) Notice: Subject to any disclaimer, the term of this patent is extended or adjusted under 35 U.S.C. 154(b) by 1379 days.

(21) Appl. No.: 10/739,124

(22) Filed: Dec. 19, 2003

(65) Prior Publication Data

US 2004/0191200 A1 Sep. 30, 2004

Related U.S. Application Data

(60) Provisional application No. 60/437,052, filed on Dec. 31, 2002.

(30) Foreign Application Priority Data

Dec. 20, 2002 (FR) ..................................... 02 16384

(51) Int. Cl.
*A61Q 1/10* (2006.01)
(52) U.S. Cl. ...................................... 424/70.7; 424/401
(58) Field of Classification Search .......................... None
See application file for complete search history.

(56) References Cited

U.S. PATENT DOCUMENTS

| | | | |
|---|---|---|---|
| 3,673,160 A | 6/1972 | Buisson et al. | |
| 3,802,841 A | 4/1974 | Robin | |
| 3,915,921 A | 10/1975 | Schlatzer, Jr. | |
| 4,071,615 A | 1/1978 | Barth | |
| 4,509,945 A | 4/1985 | Kramann et al. | |
| 5,156,911 A | 10/1992 | Stewart | |
| 5,356,627 A * | 10/1994 | Da Cunha et al. | 424/401 |
| 5,472,798 A | 12/1995 | Kumazawa et al. | |
| 5,519,063 A | 5/1996 | Mondet et al. | |
| 5,601,808 A | 2/1997 | Mellul et al. | |
| 5,736,125 A | 4/1998 | Morawsky et al. | |
| 5,756,635 A | 5/1998 | Michaud et al. | |
| 5,849,278 A * | 12/1998 | Piot et al. | 424/70.7 |
| 5,911,973 A * | 6/1999 | de la Poterie | 424/61 |
| 6,180,123 B1 | 1/2001 | Mondet | |
| 6,238,654 B1 | 5/2001 | Tournilhac et al. | |
| 6,258,916 B1 | 7/2001 | Michaud et al. | |
| 6,372,235 B1 | 4/2002 | Livoreil et al. | |
| 6,946,123 B2 | 9/2005 | De La Poterie et al. | |
| 6,979,469 B2 * | 12/2005 | Ferrari et al. | 424/707 |
| 7,029,662 B2 | 4/2006 | Auguste et al. | |
| 7,189,388 B2 | 3/2007 | Auguste et al. | |
| 2002/0085986 A1 | 7/2002 | De La Poterie et al. | |
| 2003/0031640 A9 | 2/2003 | De La Poterie et al. | |
| 2003/0078330 A1 | 4/2003 | Legrand et al. | |
| 2003/0134761 A1 | 7/2003 | Sebillotte-Arnaud et al. | |
| 2003/0191271 A1 | 10/2003 | Mondet et al. | |
| 2004/0022752 A1 | 2/2004 | De La Poterie | |
| 2004/0091447 A1 | 5/2004 | Pays et al. | |
| 2005/0260151 A1 | 11/2005 | Pays et al. | |

FOREIGN PATENT DOCUMENTS

| | | |
|---|---|---|
| EP | 0 216 479 B2 | 4/1987 |
| EP | 0 686 858 B1 | 12/1995 |
| EP | 1 086 683 B1 | 3/2001 |
| EP | 1 281 384 A1 | 2/2003 |
| EP | 1 281 385 A1 | 2/2003 |
| EP | 1 396 256 A2 | 3/2004 |
| EP | 1 417 951 A1 | 5/2004 |
| WO | WO 93/23008 | 11/1993 |
| WO | WO 01/19333 A1 | 3/2001 |
| WO | WO 02/47625 * | 6/2002 |

OTHER PUBLICATIONS

English language Derwent Abstract of EP 0 638 307, Feb. 15, 1995.
English language Derwent Abstract of EP 0 953 332, Nov. 3, 1999.
G. Fonnum et al., "Associative thickeners. Part I: Synthesis, rheology and aggregation behavior," Colloid & Polymer Science, vol. 271, No. 4, pp. 380-389 (1993).
H.C. Van de Hulst, "Rigorous Scattering Theory for Spheres of Arbitrary Size (MIE Theory)," Light Scattering by Small Particles, John Wiley & Sons, Inc., pp. 117-171 (1957).
Shuichi Nojima, "Melting Behavior of Poly($\epsilon$-caprolactone)-*block*-Polybutadiene Copolymer," Macromolecules, vol. 32, pp. 3727-3734 (1999).
B. Boutevin et al., "Study of Morphological and Mechanical Properties of PP/PBT Blends," Polymer Bulletin, vol. 34, pp. 117-123 (1995).
Pratima Rangarajan et al., "Morphology of Semicrystalline Block Copolymers of Ethylene—(Ethylene-*alt*- propylene)," Macromolecules, vol. 26, pp. 4640-4645 (1993).
D. Richter, "Polymer Aggregates with Crystalline Cores: The System Polyethylene—Poly(ethylenepropylene)," Macromolecules, vol. 30, pp. 1053-1068 (1997).
I.W. Hamley, "Crystallization in Block Copolymers," Advances in Polymer Science, vol. 148, pp. 113-137 (1999).
P. Terech, "Low-molecular weight organogelators," Specialist Surfactants, Blackie Academic & Professional, pp. 208-268 (1997).
English language abstract of EP 1 086 945 B1, Mar. 28, 2001.
English language abstract of FR 2 777 455 A1, Oct. 22, 1999.
English language abstract of FR 2 782 267 A1, Feb. 18, 2000.
English language abstract of FR 2 792 830 A1, Nov. 3, 2000.
English language abstract of JP 11-322544, Nov. 24, 1999.
English language abstract of JP 2000-63240, Feb. 29, 2000.
English language abstract of JP 2000-336016, Dec. 5, 2000.
English Translation of Japanese Office Action for Japanese Patent Application No. 2003-423608, dated Nov. 9, 2010.
English language abstract of EP 1 417 951 from esp@cenet (May 2004).
EP 1,396,256 Abstract (Mar. 2004).

* cited by examiner

*Primary Examiner* — Jyothsna Venkat
(74) *Attorney, Agent, or Firm* — Finnegan, Henderson, Farabow, Garrett & Dunner, LLP (57) ABSTRACT

Disclosed herein is a cosmetic composition for coating keratin fibers, comprising, in a physiologically acceptable aqueous medium, at least one thickener, wherein the composition has a threading nature dmax of greater than or equal to 12 mm, as well as a method for obtaining at least one effect chosen from a smooth and uniform film deposited on keratin fibers, a lengthening effect, and a separating effect, comprising applying the composition to the keratin fibers.

15 Claims, 1 Drawing Sheet

FIG. 1

COMPOSITION FOR COATING KERATIN FIBRES HAVING A THREADING NATURE

This application claims benefit of U.S. Provisional Application No. 60/437,052, filed Dec. 31, 2002.

The present disclosure relates to a cosmetic composition comprising at least one thickener, wherein the composition has a threading nature dmax of greater than or equal to 12 mm. This composition may be used for coating keratin fibres such as human eyelashes, eyebrows and hair, or alternatively false keratin fibres, such as false eyelashes.

The composition may be, for example, a makeup product for keratin fibres, a makeup base for keratin fibres such as the eyelashes, also known as a basecoat, a product to be applied over makeup, also known as a topcoat, or a cosmetic product for treating keratin fibres, or alternatively a product for the eyebrows. Further, for example, the composition may be a makeup product for the eyelashes, also known as a mascara.

Compositions for coating the eyelashes, also known as mascaras, may generally comprise, for example, at least one dry extract that comprises a dispersed fatty phase comprising at least one wax in order to give substance to the eyelashes, and also a coating on the eyelashes, and thus may result in a volumizing makeup result (i.e., the eyelash makeup may be more or less thick).

However, increasing the dry extract in a composition may result in an increase in the thickness of the composition and poor dispersion of the solid particles. As a result, the makeup film may have a granular, non-uniform appearance and may form blobs on the eyelashes. The makeup result finally obtained may be unattractive.

Furthermore, these compositions may not make it possible to obtain a satisfactory lengthening effect of the eyelashes.

There is thus a need for a composition for coating keratin fibres, for example, the eyelashes, which may make it possible to obtain good lengthening of the eyelashes, and which may deposit a smooth, uniform film of composition onto the keratin fibres.

To satisfy at least one of the requirements mentioned above, disclosed herein is a makeup composition for keratin fibres, for example, the eyelashes, which may provide a smooth and uniform film of makeup and may also make it possible to obtain a lengthening effect on the eyelashes.

The inventors have surprisingly discovered that the composition can be made and comprises at least one thickener and has a threading nature as defined in paragraph [002].

Disclosed herein is thus a cosmetic composition for coating keratin fibres, comprising, in a physiologically acceptable aqueous medium, at least one thickener, wherein the composition has a threading nature dmax of greater than or equal to 12 mm.

The threading nature represents the ability of the composition according to the disclosure to form, during application to keratin fibres, threads which, once they have been drawn with a brush, may be sufficiently consistent and conserve their shape. For example, after application, these threads, in an embodiment of the invention, do not shrink, do not break and do not collapse under the action of their own weight. These threads may be formed in the continuation of each eyelash and make it possible to obtain a noteworthy lengthening effect.

Further disclosed herein is a cosmetic treatment or makeup process for keratin fibres, comprising applying to the keratin fibres the cosmetic composition as described above.

Further disclosed herein is the use of a cosmetic composition as described above to obtain at least one result chosen from a smooth and uniform film deposited on keratin fibres, a lengthening effect, and a separating effect.

Even further disclosed herein is the use, in a cosmetic composition for coating keratin fibres, of a physiologically acceptable aqueous medium and of at least one thickener, wherein said composition has a threading nature dmax of greater than or equal to 12 mm, to obtain at least one result chosen from a smooth and uniform film deposited on the keratin fibres, a lengthening effect, and a separating effect.

The expression "physiologically acceptable aqueous medium" means a non-toxic aqueous medium that is compatible with keratin fibres, for example, human eyelashes, eyebrows, and hair, and further for example, the area around the eyes.

Measurement of the Threading Nature

The threading nature of the composition is determined at room temperature (25° C.) using the texturometer sold under the name TA X-T2i by the company RHEO, equipped with a stainless-steel cylindrical spindle 1.2 cm in diameter, by imposing a vertical, displacement of the spindle into a sample of the composition (contained in a cup 3.2 cm in diameter filled to the maximum, wherein the excess composition is leveled off at the surface) and by measuring the change in the force (compression force or stretching force) as a function of time.

The protocol is as follows:

The spindle is displaced at a speed of 1 mm/s and penetrates the composition to, a penetration depth of 0.2 mm. The spindle is kept still for 1 second (corresponding to the relaxation phase) and is then withdrawn at a speed of 10 mm/s.

During the relaxation phase, the force (compression force) decreases strongly until it reaches zero, and, during the withdrawal of the spindle (withdrawal phase), the force (stretching force) then becomes negative and subsequently rises again until it reaches the value 0.

During the withdrawal phase, a thread of composition forms between the surface of the composition and the spindle, the length of the thread increasing until it reaches its maximum before breaking. The threading nature or dmax (expressed in mm) corresponds to the maximum length of the thread before breaking, which is equivalent to the distance covered by the spindle during this withdrawal phase.

$$d_{max}(\text{mm}) = \text{withdrawal time (s)} \times \text{withdrawal speed (mm/s)}$$

The withdrawal time is the time elapsed between the withdrawal of the spindle from the sample (formation of the thread of composition) and the breaking of the thread.

The measurements of the threading nature are repeated three times for the same composition.

The composition according to the disclosure has a threading nature dmax of greater than or equal to 12 mm, ranging, for example, from 12 to 35 mm, such as from 15 to 32 mm. The composition having such a threading nature according to the disclosure can make it possible, during application to keratin fibres, such as the eyelashes, using a brush, to form a thread of composition in the continuation of the eyelash. After application to the eyelash, this thread can maintain its shape and not shrink, thus producing a lengthening effect of the eyelash.

The composition according to the disclosure may have certain rheological behaviour, defined, for example, by the viscoelastic properties. It may also have certain flow profile, as described below.

Measurement of the Rheological Properties

The measurements are performed on an RS 75 controlled-stress rheometer from the company ThermoRhéo, equipped with a thermostatically maintained bath and a stainless-steel spindle of plate/plate geometry, the plate having a diameter of 20 mm and a gap (distance between the bottom plate—known as the stator plate—on which the composition is deposited and the top plate—known as the rotor plate) of 0.3 mm. The two plates are striated to limit the sliding phenomena at the walls of the plates.

The measurements are performed at 25° C.±0.5° C.

Measurement of the Viscoelastic Properties

In one aspect, the compositions in accordance with the disclosure may show certain viscoelastic behaviour.

In general, a material is said to be viscoelastic when, under the effect of shear, it has both the characteristics of an elastic material, i.e., the capability to store energy, and the characteristics of a viscous material, i.e., the capability to dissipate energy.

For example, the viscoelastic behaviour of compositions of the disclosure may be characterized by its elasticity $\delta$ (expressed in degrees) corresponding to the dephasing angle between the applied stress and the recorded strain. This parameter is defined, for example, in the publication "Initiation à la rhéologie [Introduction to Rheology]", G. Couarraze and J. L. Grossiord, 2nd edition, 1991, published by Lavoisier-Tec 1 Doc.

For example, the viscoelastic behaviour of the compositions according to the disclosure may be characterized by a plateau elasticity $\delta_p$ of greater than or equal to 36°, for example, ranging from 36° to 75°, and further for example, from 45° to 58°.

The dynamic measurements are performed by applying a harmonic variation of the stress. In these experiments, the magnitudes of the shear stress (noted as $\tau$) and of the shear strain (noted as $\gamma$) are low so as to remain within the limits of the linear viscoelastic domain of the composition (conditions for evaluating the rheological characteristics of the composition at rest).

The linear viscoelastic domain is generally defined by the fact that the response of the material (i.e. the strain) is at any moment directly proportional to the value of the applied force (i.e. the stress). In this domain, the applied stresses are small and the material undergoes strains without modifying its microscopic structure. Under these conditions, the material is studied "at rest" and non-destructively.

The composition is subjected to a harmonic shear according to a stress $\tau(t)$ varying sinusoidally according to a pulse $\omega$ ($\omega=2\pi\nu$, wherein $\nu$ is the frequency of the applied shear). The composition thus sheared undergoes a stress $\tau(t)$ and responds according to a strain $\gamma(t)$ corresponding to micro-strains for which the modulus of rigidity varies little as a function of the imposed stress, wherein t is time.

The stress $\tau(t)$ and the strain $\gamma(t)$ are defined, respectively, by the following relationships:

$$\tau(t)=\tau_0 \cos(\omega \cdot t)\ \gamma(t)=\gamma_0 \cos(\omega \cdot t - \delta)$$

wherein $\tau_0$ is the maximum amplitude of the stress and $\gamma_0$ is the maximum amplitude of the strain. The elasticity $\delta$ is the dephasing angle between the stress and the strain. The measurements are performed at a frequency of 1 Hz ($\nu=1$ Hz).

The change in the stiffness modulus G (corresponding to the ratio of $\tau_0$ to $\gamma_0$) and of the elasticity $\delta$ (corresponding to the dephasing angle of the applied stress relative to the measured strain) is thus measured as a function of the applied stress $\tau(t)$.

The strain of the composition for the stress zone in which the variation of the elasticity $\delta$ is less than 10% (i.e. the microstrain region) is, for example, measured, and the "plateau" parameter $\delta_p$ is thus determined.

Measurement of the Flow Profile

In another aspect, the composition according to the disclosure may have a rheological profile such that, for a shear rate range ranging from $10^{-2}$ to $10^3$ s$^{-1}$, the ratios of the variation in the shear rate to the variation in the applied shear stress $$\text{(noted as } \frac{\Delta\dot{\gamma}}{\Delta\tau}\text{)}$$

are not more than 7, wherein the composition is capable of undergoing shear stresses without fracturing in the shear rate range.

The analysis in the flow regime at equilibrium comprises subjecting the sample, from a given moment, to an instantaneous shear stress $\tau$ (shear), which is kept constant for a time t (this waiting time is chosen such that the permanent regime is reached at t=30 s). Simultaneously, the change over time of the corresponding shear strain $\gamma$ is monitored and the shear rate $\dot{\gamma}$ when equilibrium is reached is recorded.

The sample is maintained at 25° C. for 2 minutes (without any applied shear).

Additionally, the flow at equilibrium is measured in controlled-stress mode.

Increasing stresses are applied on the sample, starting from an initial stress equal to 0.64 Pa, to arrive at a final stress of 2000 Pa, wherein the stresses are applied only once.

Time is allowed for a stable value to be obtained between each stress and the waiting time between each stress is 30 s.

For example, the shear rate range may be from $10^{-4}$ s$^{-1}$ to $10^3$ s$^{-1}$. In this range, the maximum value of $10^3$ s$^{-1}$ should be taken into account with a measurement uncertainty of ±150 s$^{-1}$.

The results are analysed by means of a graphical representation of the change in viscosity, noted as $\eta$, as a function of the shear rate, noted as $\dot{\gamma}$. Such a graph may show a first plateau region, known as the first Newtonian region, defined for small values of $\dot{\gamma}$ (e.g. $\dot{\gamma} \leq 10^{-3}$ s$^{-1}$) in which the viscosity remains constant. This region is representative of the viscosity of the product at rest.

For higher shear rates, e.g. $10^{-2}$ s$^{-1} \leq \dot{\gamma} \leq 10^3$ s$^{-1}$, the viscosity drops, and the product becomes fluid setting into motion to flow. In this shear window, two types of behaviours may be seen:

(1) either the flow is uniform, in which case there is equidistance between the points of the graph and the curve corresponds to a ratio:

$$\frac{\Delta\dot{\gamma}}{\Delta\tau} \leq 7$$

or (2) the flow is non-uniform, in which case there is no longer continuity or equidistance between the points of the graph and the curve corresponds to a ratio:

$$\frac{\Delta\dot{\gamma}}{\Delta\tau} > 7$$

In one aspect, the composition according to the disclosure may have a rheological profile such that, for a shear rate range ranging from $10^{-2}$ to $10^3$ s$^{-1}$, the ratios of the variation in the shear rate to the variation in the applied shear stress (noted as $\frac{\Delta\dot{\gamma}}{\Delta\tau}$)

are not more than 7, wherein the composition is capable of undergoing shear stresses without fracturing in the shear rate range.

The compositions that have such characteristics may show continuous (i.e., without fracturing) and uniform (i.e., without formation of blobs) flow. Such compositions, when applied to keratin fibres, may give a smooth and uniform deposit on the keratin fibres.

Physiologically Acceptable Aqueous Medium

The physiologically acceptable aqueous, medium of the compositions according to the disclosure is continuous aqueous medium, i.e., water or a mixture of water with at least one water-miscible organic solvent.

The aqueous medium of the composition may thus comprise a mixture of water and of at least one water-miscible organic solvent chosen, for example, from lower monoalcohols comprising from 1 to 5 carbon atoms, for example ethanol and isopropanol, glycols comprising from 2 to 8 carbon atoms, for example glycerol, propylene glycol, ethylene glycol, 1,3-butylene glycol and dipropylene glycol, $C_3$-$C_4$ ketones, and $C_2$-$C_4$ aldehydes. The aqueous medium (water and optionally the at least one water-miscible organic solvent) may be present in an amount ranging, for example, from 10% to 80% by weight, such as from 20% to 70% by weight and further such as from 30% to 60% by weight, relative to the total weight of the composition.

Thickener

In one aspect, the at least one thickener of the composition according to the disclosure may be chosen, for example, from shear-thinning thickeners, i.e., an agent capable of giving the composition containing it shear-thinning behaviour, characterized in that the viscosity of the composition decreases when increasing shears are applied to the composition.

In one embodiment, the at least one thickener may be chosen from associative polymers.

For the purposes of the present disclosure, the term "associative polymer" means any amphiphilic polymer comprising, in its structure, at least one fatty chain and at least one hydrophilic portion.

The associative polymers in accordance with the present disclosure may be chosen from anionic, cationic, nonionic and amphoteric polymers.

Among the associative anionic polymers that non-limiting mention may be made of those comprising at least one hydrophilic unit and at least one fatty-chain allyl ether unit, for example, those in which the at least one hydrophilic unit comprises at least one ethylenic unsaturated anionic monomeric residue chosen, for example, from the residue of a vinylcarboxylic acid, the residue of an acrylic acid, and the residue of a methacrylic acid, and in which the at least one fatty-chain allyl ether unit is chosen from the residues of the monomers of formula (I) below:

CH$_2$=C(R')CH$_2$OB$_n$R (I)

wherein R' is chosen from H and CH$_3$, B is an ethylenoxy radical, n is 0 or an integer ranging from 1 to 100, and R is chosen from hydrocarbon-based radicals chosen from alkyl, arylalkyl, aryl, alkylaryl and cycloalkyl radicals comprising from 8 to 30 carbon atoms, for example, from 10 to 24 and further for example from 12 to 18 carbon atoms.

Anionic amphiphilic polymers of this type are described and prepared, for example, according to an emulsion polymerization process described in document EP-0 216 479.

Associative anionic polymers that non-limiting mention may be made include anionic polymers comprising at least one hydrophilic unit of olefinic unsaturated carboxylic acid type, and at least one hydrophobic unit exclusively of ($C_{10}$-$C_{30}$)alkyl ester of unsaturated carboxylic acid type.

Further examples include the anionic polymers described and prepared according to U.S. Pat. Nos. 3,915,921 and 4,509,949.

Cationic associative polymers that non-limiting mention may be made include quaternized cellulose derivatives and polyacrylates comprising at least one amine side group.

The nonionic associative polymers may be chosen from at least one of:
 celluloses modified with groups comprising at least one fatty chain, for example hydroxyethylcelluloses modified with groups comprising at least one fatty chain, such as alkyl groups, for example $C_8$-$C_2$, arylalkyl and alkylaryl groups, for example Natrosol Plus Grade 330 CS($C_{1-6}$ alkyls) sold by the company Aqualon,
 celluloses modified with polyalkylene glycol alkylphenyl ether groups,
 guars, for example hydroxypropyl guar, modified with groups comprising at least one fatty chain, for example an alkyl chain,
 copolymers of vinylpyrrolidone and of fatty-chain hydrophobic monomeric residues,
 copolymers of at least one monomeric residue chosen from $C_1$-$C_6$ alkyl methacrylates and acrylates and of amphiphilic monomeric residues comprising at least one fatty chain,
 copolymers of monomeric residues chosen from hydrophilic methacrylates and acrylates and of hydrophobic monomeric residues comprising at least one fatty chain, for example the polyethylene glycol methacrylate/lauryl methacrylate copolymer,
 associative polyurethanes, and
 mixtures thereof.

For example, the associative polymers may be chosen from associative polyurethanes.

In another example, associative polyurethanes may be chosen from nonionic block copolymers comprising in the chain both hydrophilic blocks usually of polyoxyethylene nature, and hydrophobic blocks that may be chosen from aliphatic sequences, cycloaliphatic sequences, and aromatic sequences.

Further for example, these polymers may comprise at least two hydrocarbon-based lipophilic chains comprising from 6 to 30 carbon atoms, separated by a hydrophilic block, wherein the hydrocarbon-based lipophilic chains may be chosen from pendant chains and chains at the end of a hydrophilic block. In yet another example, the polymers may comprise at least one pendant chain. In another example, the polymers may comprise a hydrocarbon-based chain at one or both ends of a hydrophilic block.

For example, the associative polyurethanes may be blocked in triblock or multiblock form. The hydrophobic blocks may thus be at each end of the chain (for example: triblock copolymer with a hydrophilic central block) or distributed both at the ends and within the chain (for example multiblock copolymer). These polymers may also be chosen from graft polymers and starburst polymers.

In another example, the associative polyurethanes are triblock copolymers in which the hydrophilic block is a polyoxyethylene chain comprising from 50 to 1000 oxyethylene groups. In general, the associative polyurethanes comprise a urethane bond between the hydrophilic blocks, hence the name.

By way of example, among the associative polymers that may be used, non-limiting mention may be made of the polymer $C_{16}$-$OE_{120}$-$C_{16}$ from the company Servo Delden (under the name SER AD FX1100, which comprises a urethane functional group and has a weight-average molecular weight of 1300), wherein OE is an oxyethylene unit. In another example, an associative polymer that may also be used is Rhéolate 205 comprising a urea functional group, sold by the company Rheox, or Rhéolate 208 or 204. These associative polyurethanes are sold in pure form.

In yet another example, the product DW 1206B from Rohm & Haas comprising a $C_{20}$ alkyl chain with a urethane bond, sold at a solids content of 20% in water, may also be used.

Further for example, it is also possible to use solutions or dispersions of these polymers, for example, in water or in aqueous-alcoholic medium. Examples of such polymers that non-limiting mention may be made include SER AD FX1010, SER AD FX1035 and SER AD 1070 from the company Servo Delden, and Rhéolate 255, Rhéolate 278 and Rhéolate 244 sold by the company. Rheox. It is also possible to use the product DW 1206F and DW 1206J, and also Acrysol RM 184 or Acrysol 44 from the company Rohm & Haas, or alternatively Borchigel LW 44 from the company Borchers.

In yet another example, the polymers that may be used include those described in the article by G. Fonnum, J. Bakke and Fk. Hansen—Colloid Polym. Sci 271, 380-389 (1993).

In one embodiment, the at least one thickener may be present in an amount ranging from 0.05% to 20% by weight of solids (or active materials), for example, from 0.2% to 10% by weight of solids and further for example, from 0.5% to 0.5% by weight of solids, relative to the total weight of the composition according to the disclosure.

Solid Particles

In one embodiment, the composition according to the disclosure may comprise an aqueous dispersion of first solid particles with a mean size of less than or equal to 700 nm.

In yet another embodiment, these first solid particles have a mean size of less than 700 nm, for example, ranging from 10 nm to 700 nm and further for example from 20 nm to 300 nm, wherein the mean size of the particles is expressed as the mean. "effective" volume diameter D[4.3] as defined below.

The solid particles may be in varied shapes. For example, the solid particles may be spherical.

These particles are dispersed in the physiologically acceptable aqueous medium of the composition.

Measurement of the Particle Sizes

The particle sizes may be measured by various techniques; for example, light-scattering techniques (dynamic and static), Coulter counter methods, sedimentation rate measurements (related to the size via Stokes' law) and microscopy. These techniques make it possible to measure a particle diameter and in some cases, also a particle size distribution.

The sizes and size distributions of the particles in the compositions according to the disclosure may be measured, for example by static light scattering using a commercial granulometer such as the MasterSizer 2000 from Malvern. The data are processed on the basis of the Mie scattering theory. This theory, which is exact for isotropic particles, makes it possible to determine an "effective" particle diameter in the case of non-spherical particles. This theory is described, for example, in the publication by Van de Hulst, H. C., "Light Scattering by Small Particles," Chapters 9 and 10, Wiley, New York, 1957.

The particles can be characterized by their mean "effective" diameter by volume D[4.3], defined in the following manner:

$$D[4.3] = \frac{\sum_i V_i \cdot d_i}{\sum_i V_i}$$

wherein: $V_i$ is the volume of the particles with an effective diameter $d_i$. This parameter is described, for example, in the technical documentation of the granulometer.

The measurements are performed at 25° C. on a dilute particle dispersion, obtained from the composition in the following manner: 1) dilution by a factor of 100 with water, 2) homogenization of the solution, 3) standing of the solution for 18 hours, and 4) recovery of the whitish uniform supernatant.

The "effective" diameter is obtained by taking a refractive index of 1.33 for water and a mean refractive index of 1.42 for the particles.

In one aspect, the composition according to the disclosure may also comprise second solid particles with a mean size of greater than or equal to 701 nm, for example, ranging from 701 nm to 50 further, for example, from 1 μm to 50 μm and even further for example, from 1 μm to 25 μm. These second solid particles are dispersed in the physiologically acceptable aqueous medium of the composition according to the disclosure.

For example, the solid particles, i.e. the first and second solid particles, may be chosen from at least one of film-forming polymers, semi-crystalline polymers, rheological agents, waxes, and pigments and fillers.

Further, for example, the first solid particles may be chosen from at least one of film-forming polymers and waxes.

In yet another example, the second solid particles may be chosen from at least one of waxes, pigments, fillers, semi-crystalline polymers and rheological agents.

Further for example, the first solid particles may be present in an amount ranging from 5% to 30% by weight, such as from 10% to 25% by weight relative to the total weight of the composition.

In another example, the second solid particles may be present in an amount ranging from 10% to 40% by weight, such as from 12% to 30% by weight relative to the total weight of the composition.

Waxes

The solid particles present in the composition according to the disclosure may comprise wax particles.

For the purposes of the present disclosure, the term "wax" means a lipophilic fatty substance, which is solid at room temperature (25° C.), undergoes a reversible solid/liquid change of state, with a melting point of greater than or equal to 30° C., may be up to 120° C., and has an anisotropic crystal organization in solid form.

For example, the waxes that may be suitable for the composition according to the disclosure may have a melting point of greater than 45° C., such as greater than 55° C.

The melting point of the wax may be measured using a differential scanning calorimeter (D.S.C.), for example the calorimeter sold under the name DSC 30 by the company Mettler.

The measuring protocol is as follows:

a sample of 15 mg of the wax placed in a crucible is subjected to a first temperature increase ranging from 0° C. to 120° C., at a heating rate of 10° C./minute, it is then cooled from 120° C. to 0° C. at a cooling rate of 10° C./minute and is finally subjected to a second temperature increase ranging from 0° C. to 120° C. at a heating rate of 5° C./minute. During the second temperature increase, the variation of the difference in power absorbed by the empty crucible and by the crucible containing the sample of the wax is measured as a function of the temperature. The melting point of the wax is the temperature value corresponding to the top of the peak of the curve representing the variation in the difference in absorbed power as a function of the temperature.

For example, the waxes that may be used in the compositions according to the disclosure may be chosen from waxes that are solid and rigid at room temperature, of animal, plant, mineral or synthetic origin.

Further, for example, the wax may also have a hardness ranging from 0.05 MPa to 15 MPa, such as from 6 MPa to 15 MPa. The hardness is determined by measuring the compressive strength, measured at 20° C. using a texturometer sold under the name TA-XT2i by the company Rheo, equipped with a stainless-steel cylinder 2 mm in diameter travelling at a measuring speed of 0.1 mm/s, and penetrating into the wax to a penetration depth of 0.3 mm.

The measuring protocol is as follows:

the wax is melted at a temperature equal to the melting point of the wax +20° C. The molten wax is cast in a container with 30 mm in diameter and 20 mm deep. The wax is recrystallized at room temperature (25° C.) over 24 hours and is then stored for at least 1 hour at 20° C. before performing the hardness measurement. The value of the hardness is the compressive strength measured divided by the area of the texturometer cylinder in contact with the wax.

For example, hydrocarbon-based waxes such as beeswax, lanolin wax and Chinese insect waxes; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may be used.

Non-limiting mention may also be made of the waxes obtained by catalytic hydrogenation of oils chosen from animal and plant oils comprising at least one fatty chain chosen from linear and branched $C_8$-$C_{32}$ fatty chains, for example hydrogenated jojoba oil, hydrogenated sunflower oil, hydrogenated castor oil, hydrogenated coconut oil and hydrogenated lanolin oil, bis(1,1,1-trimethylolpropane) tetrastearate sold under the name "Hest 2T-4S" by the company Heterene and bis(1,1,1-trimethylolpropane) tetrabehenate sold under the name Hest 2T-4B by the company Heterene. Non-limiting mention may also be made of silicone waxes and fluoro waxes, and mixtures thereof.

For instance, the composition according to the disclosure may comprise from 1% to 40% by weight of waxes; for example, it may comprise from 5% to 30% and further for example from 5% to 20% by weight of waxes relative to the total weight of the composition.

For example, the wax particles in aqueous dispersion may have a size ranging from 10 nm to 50 µm.

For instance, the first solid particles may be chosen from wax particles, which may be present in the form of an aqueous microdispersion of particles of at least one wax, and which may have a mean size of less than or equal to 700 nm, for example from 10 nm to 700 nm, further for example, from 30 nm to 500 nm and still further for example, from 50 nm to 200 nm.

The composition may thus comprise a mixture of the first solid particles of at least one wax with a size ranging from 10 nm to 50 µm as described above, and of the second solid particles of at least one wax with a mean size ranging from 1 µm to 50 µm, such as from 1 µm to 25 µm.

Film-Forming Polymers

The solid particles present in the composition according to the disclosure may comprise particles of at least one film-forming polymer in aqueous dispersion. Such a dispersion is generally known as a latex or pseudolatex.

In one aspect, the composition according to the disclosure may comprise particles of at least one film-forming polymer.

In the present disclosure, the term "film-forming polymer" means a polymer capable of forming, by itself or in the presence of at least one auxiliary film-forming agent, a continuous film that adheres to a support, for example, keratin fibres, such as the eyelashes.

Among the film-forming polymers that may be used in the composition of the present disclosure, non-limiting mention may be made of synthetic polymers, of free-radical type or of polycondensate type, and of polymers of natural origin, and mixtures thereof.

The expression "free-radical film-forming polymer" means a polymer obtained by polymerization of unsaturated monomers; such as ethylenically unsaturated monomers, wherein each monomer is capable of homopolymerizing (unlike polycondensates).

For example, the free-radical film-forming polymers may be chosen from vinyl polymers and copolymers, such as acrylic polymers.

Further for example, the vinyl film-forming polymers may result from the polymerization of ethylenically unsaturated monomers comprising at least one group chosen from acid groups, the esters thereof, and the amides thereof.

For instance, monomers comprising at least one acidic group that may be used include $\alpha,\beta$-ethylenic unsaturated carboxylic acids, such as acrylic acid, methacrylic acid, crotonic acid, maleic acid and itaconic acid, and mixtures thereof. For example, (meth)acrylic acid and crotonic acid may be used; and in one embodiment, (meth)acrylic acid is used.

For instance, the esters of the acidic groups may be chosen from the esters of (meth)acrylic acid (also known as (meth) acrylates), such as alkyl (meth)acrylates, for example $C_1$-$C_{30}$ such as $C_1$-$C_{20}$ alkyl, aryl (meth)acrylates, further for example, $C_6$-$C_{10}$ aryl, and hydroxyalkyl (meth)acrylates, and even further for example, $C_2$-$C_6$ hydroxyalkyl (meth)acrylates.

Among the alkyl (meth)acrylates that may be used, non-limiting mention may be made of methyl methacrylate, ethyl methacrylate, butyl methacrylate, isobutyl methacrylate, 2-ethylhexyl methacrylate, lauryl methacrylate and cyclohexyl methacrylate, and mixtures thereof.

Among the hydroxyalkyl (meth)acrylates that may be used, non-limiting mention may be made of hydroxyethyl acrylate, 2-hydroxypropyl acrylate, hydroxyethyl methacrylate and 2-hydroxypropyl methacrylate.

Among the aryl (meth)acrylates that may be used, non-limiting mention may be made of benzyl acrylate and phenyl acrylate.

In one example, the (meth)acrylic acid esters may be alkyl (meth)acrylates.

In one aspect of the present disclosure, the alkyl group of the esters may be either fluorinated or perfluorinated, i.e., some or all of the hydrogen atoms of the alkyl group are replaced with fluorine atoms.

Non-limiting examples of the amides of the acidic groups that may be mentioned include (meth)acrylamides, such as N-alkyl (meth)acrylamides, for example, $C_2$-$C_{12}$ alkyl (meth)

acrylamides. Among N-alkyl (meth)acrylamides, non-limiting mention may be made of N-ethylacrylamide, N-t-butylacrylamide, N-t-octylacrylamide and N-undecylacrylamide.

For example, the vinyl film-forming polymers may also result from the homopolymerization or copolymerization of monomers chosen from vinyl esters and styrene monomers. Further for example, these monomers may be polymerized with monomers chosen from acidic monomers, the esters thereof, and the amides thereof, such as those mentioned above.

Non-limiting examples of the vinyl esters that may be mentioned include vinyl acetate, vinyl neodecanoate, vinyl pivalate, vinyl benzoate and vinyl t-butylbenzoate, and mixtures thereof.

Non-limiting examples of styrene monomers that may be mentioned include styrene and α-methylstyrene.

The above lists of monomers are not limiting, and it is possible to use any monomer known to those skilled in the art that falls within the categories of acrylic and vinyl monomers (including monomers modified with at least one silicone chain).

Among the acrylic film-forming polymers that may be used, non-limiting mention may be made of those sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® and Dow Latex 424® by the company Dow Chemical, Daitosol 5000 AD by the company Daito Kasey Kogyo, and "Syntran® 5190" "Syntran® 5760" and "Syntran® 5009" by the company Interpolymer.

Non-limiting examples of film-forming polycondensates that may also be mentioned include polyurethanes, polyesters, polyesteramides, fatty-chain polyesters, polyamides and epoxyester resins. In one embodiment, polyurethanes are used.

For example, the polyurethanes may be chosen from at least one of anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes.

Further for example, the film-forming polyurethane may be chosen from aliphatic, cycloaliphatic and aromatic polyurethanes, polyurea-urethane and polyurea copolymers, comprising at least one block chosen from:
　　at least one block chosen from aliphatic, cycloaliphatic and aromatic polyester origins,
　　at least one silicone block chosen from branched and non-branched silicone blocks, for example polydimethylsiloxane and polymethylphenylsiloxane, and
　　at least one block comprising at least one fluoro group.

The film-forming polyurethanes that may be used may also be obtained from branched or non-branched polyesters, or from alkyls comprising labile hydrogens that are modified by reaction with a diisocyanate and a difunctional organic compound (for example dihydro, diamino or hydroxyamino), and comprising either a carboxylic acid or carboxylate group, or a sulphonic acid or sulphonate group, or alternatively a neutralizable tertiary amine group or a quaternary ammonium group.

For example, the film-forming polyurethanes that may be used include those manufactured or sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, and Impranil 85® by the company Bayer, and mixtures thereof.

For instance, the polyesters may be obtained, in a known manner, by polycondensation of dicarboxylic acids with polyols, such as diols.

The dicarboxylic acid may be aliphatic, alicyclic or aromatic. Non-limiting examples of such acids that may be mentioned include: oxalic acid, malonic acid, dimethylmalonic acid, succinic acid, glutaric acid, adipic acid, pimelic acid, 2,2-dimethylglutaric acid, azeleic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, and 2,6-naphthalenedicarboxylic acid, and mixtures thereof. These dicarboxylic acid monomers may be used alone or as a combination of at least two dicarboxylic acid monomers. Examples of these monomers include phthalic acid, isophthalic acid, and terephthalic acid.

For example, the diol may be chosen from aliphatic, alicyclic and aromatic diols. Further for example, the diol may be chosen from ethylene glycol, diethylene glycol, triethylene glycol, 1,3-propanediol, cyclohexanedimethanol and 4-butanediol, and mixtures thereof.

In another example, other polyols that may be used include glycerol, pentaerythritol, sorbitol and trimethylolpropane.

The polyesteramides may be obtained in a manner similar to that of the polyesters, by polycondensation of diacids with diamines or with amino alcohols. For example, diamines that may be used include ethylenediamine, hexamethylenediamine and meta- or para-phenylenediamine. Further for example, an amino alcohol that may be used is monoethanolamine.

The polyester may also comprise at least one monomeric residue comprising at least one group chosen from group of —$SO_3M$, wherein M is chosen from a hydrogen atom, an ammonium ion $NH_4^+$, and metal ions, for example $Na^+$, $Li^+$, $K^+$, $Mg^{2+}$, $Ca^{2+}$, $Cu^{2+}$, $Fe^{2+}$ and $Fe^{3+}$ ions. In one embodiment, a difunctional aromatic monomer comprising such a group —$SO_3M$ may be used.

The aromatic nucleus of the difunctional aromatic monomer comprising a group —$SO_3M$ as described above may be chosen, for example, from benzene, naphthalene, anthracene, diphenyl, oxydiphenyl, sulphonyldiphenyl and methylenediphenyl ring systems. Non-limiting examples of difunctional aromatic monomers comprising a group —$SO_3M$ that may be mentioned include: sulphoisophthalic acid, sulphoterephthalic acid, sulphophthalic acid and 4-sulphonaphthalene-2,7-dicarboxylic acid, and mixtures thereof. Copolymers based on isophthalate/sulphoisophthalate, for example copolymers obtained by condensation of diethylene glycol, cyclohexanedimethanol, isophthalic acid and sulphoisophthalic acid, and mixtures thereof, may be used in the compositions disclosed herein. Such polymers are sold, for example, under the brand name Eastman AQ by the company Eastman Chemical Products.

The polymers of natural origin, which are optionally modified, may be chosen from shellac resin, sandarac gum, dammar resins, elemis gums, copal resins, and water-insoluble cellulose polymers, and mixtures thereof.

Non-limiting mention may also be made of the polymers resulting from the free-radical polymerization of at least one free-radical monomer inside and/or partially at the surface of pre-existing particles of at least one polymer chosen from polyurethanes, polyureas, polyesters, polyesteramides and alkyds. These polymers are generally known as hybrid polymers.

For example, the film-forming polymer may be chosen from film-forming polyurethanes, the film-forming polyacrylics described above, and mixtures thereof.

The aqueous dispersion of particles of the at least one film-forming polymers may be prepared by a person skilled in the art on the basis of his general knowledge.

For instance, the at least one film-forming polymer in aqueous dispersion may be present in the composition according to the disclosure in a solids content (or active materials content) of the polymer ranging from 0.1% to 30% by weight, for example from 1% to 15% by weight and further for example from 2% to 10% by weight, relative to the total weight of the composition.

In another instance, the size of the particles of film-forming polymers in aqueous dispersion may range from 10 nm to 700 nm, for example from 20 nm to 300 nm and further for example from 25 nm to 150 nm.

The composition according to the disclosure may also comprise at least one auxiliary film-forming agent that can promote the formation of a film with the particles of the at least one film-forming polymer. Such at least one film-forming agent may be chosen from any agents known to those skilled in the art as being capable of satisfying the desired function, such as plasticizers and coalescers.

Semi-Crystalline Polymer

In one aspect, the solid particles present in the composition according to the disclosure may comprise particles (second particles) of at least one semi-crystalline polymer in aqueous dispersion.

The term "semi-crystalline polymer" means a polymer comprising a crystallizable portion, such as a crystallizable pendent chain or a crystallizable block in the polymer skeleton, and an amorphous portion in the polymer skeleton, and having a temperature of first-order reversible phase change, such as the melting point (solid-liquid transition). When the crystallizable portion is in the form of a crystallizable block of the polymer skeleton, the amorphous portion of the polymer is in the form of an amorphous block; in this case, the semi-crystalline polymer is a block copolymer chosen, for example, from the diblock, triblock and multiblock type copolymers, comprising at least one crystallizable block and at least one amorphous block. The term "block" generally means at least 5 identical repeating units. The crystallizable block(s) are then of different chemical nature from the amorphous block(s).

In one embodiment, the semi-crystalline polymer according to the disclosure has a melting point of greater than or equal to 30° C., for example ranging from 30° C. to 80° C. and further for example from 30° C. to 60° C. This melting point is a temperature of first-order change of state.

This melting point may be measured by any known method, for example, via differential scanning calorimetry (DSC).

For example, the at least one semi-crystalline polymer has a number-average molecular mass $\overline{M}n$ of greater than or equal to 1000, ranging, for example, from 2000 to 800 000, further for example from 3000 to 500 000, even further for example from 4000 to 150 000. The number-average molecular mass of the at least one semi-crystalline polymer disclosed herein may, for example, be less than 100 000; for example, from 4000 to 99 000. In one embodiment, the at least one semi-crystalline polymer disclosed herein has a number-average molecular mass of greater than 5600, for example ranging from 5700 to 99 000.

For the purposes of the disclosure, the expression "crystallizable chain or block" means a chain or block which, if it were obtained alone, would change from the amorphous state to the crystalline state reversibly, depending on whether one is above or below the melting point. As disclosed herein, a "chain" is a group of atoms, which are pendent or lateral relative to the polymer skeleton. A "block" is a group of atoms belonging to the polymer skeleton, wherein this group constitutes one of the repeating units of the polymer. In one embodiment, the "pendent crystallizable chain" may be a chain comprising at least 6 carbon atoms.

For instance, the crystallizable blocks or chains of the semi-crystalline polymers may be present in an amount of at least 30% of the total weight of each polymer, for example at least 40%. The semi-crystalline polymers of the disclosure comprising crystallizable blocks may be block or multiblock polymers. They may be obtained by polymerizing a monomer comprising reactive (or ethylenic) double bonds or by polycondensation. When the semi-crystalline polymers of the disclosure are polymers comprising crystallizable pendent chains, these pendent chains' may be, for example, in random or statistical form.

In one embodiment, the semi-crystalline polymers of the disclosure may be of synthetic origin. Moreover, they do not comprise a polysaccharide skeleton. In general, the crystallizable units (chains or blocks) of the semi-crystalline polymers according to the disclosure may originate from monomers comprising crystallizable blocks or chains, used for the manufacture of the semi-crystalline polymers.

For example, the semi-crystalline polymers that may be used may be chosen from:

- block copolymers of polyolefins with controlled crystallization, such as those whose monomers are described in EP-A-0 951 897,
- polycondensates, such, as those chosen from aliphatic and aromatic polyester types and aliphatic/aromatic copolyester types,
- homopolymers and copolymers comprising at least one crystallizable pendent chain and homopolymers and copolymers comprising at least one crystallizable block in the skeleton, such as those described in U.S. Pat. No. 5,156,911,
- homopolymers and copolymers comprising at least one crystallizable pendent chain, such as those comprising at least one fluoro group, as described in document WO-A-01/19333,
- and mixtures thereof.

In the last two cases, the homopolymers and copolymers, the at least one crystallizable pendent chain or block may be hydrophobic.

A) Semi-Crystalline Polymers Comprising at Least One Crystallizable Pendent Chain Non-limiting mention may be made, for example, of those defined in U.S. Pat. No. 5,156,911 and document WO-A-01/19333. They are homopolymers or copolymers comprising from 50% to 100% by weight of units resulting from the polymerization of at least one monomer bearing at least one crystallizable hydrophobic pendent chain.

These homopolymers or copolymers are of any nature, provided that they meet the conditions mentioned previously.

They can result:

- from the polymerization, such as the free-radical polymerization, of at least one monomer comprising at least one double bond chosen from reactive and ethylenic double bonds with respect to a polymerization, such as a vinyl, (meth)acrylic or allylic group, and
- from the polycondensation of at least one monomer comprising at least one co-reactive group chosen, for example, from carboxylic acid, sulphonic acid, alcohol, amine and isocyanate, such as polyesters, polyurethanes, polyethers, polyureas and polyamides.

In general, these polymers may be chosen, for example, from homopolymers and copolymers resulting from the polymerization of at least one monomer comprising at least one crystallizable chain of formula X:

(X)

wherein M is an atom of the polymer skeleton, S is a spacer and C is a crystallizable group.

For example, the crystallizable chains "—S—C" may be aliphatic or aromatic, and optionally fluorinated and perfluorinated. "S" may, for example, be a group chosen from $(CH_2)_m$, $(CH_2CH_2O)_m$ and $(CH_2O)$, which may be linear or branched or cyclic, with n is an integer ranging from 0 to 22. "S" may, for example, be a linear group. "S" and "C" may be different.

When the crystallizable chains "—S—C" are hydrocarbon-based aliphatic chains, they comprise at least one hydrocarbon-based alkyl chain comprising at least 11 carbon atoms and not more than 40 carbon atoms, for example, not more than 24 carbon atoms. They may, for example, be aliphatic chains or alkyl chains comprising at least 12 carbon atoms, such as $C_{14}$-$C_{24}$ alkyl chains. When they are fluoroalkyl and perfluoroalkyl chains, they may comprise at least six fluorinated carbon atoms, for example at least 11 carbon atoms, at least six of which are fluorinated.

Non-limiting examples of semi-crystalline polymers or copolymers comprising at least one crystallizable chain that may be mentioned include those resulting from the polymerization of at least one monomer chosen from: (meth)acrylates of saturated alkyl comprising at least one $C_{14}$-$C_{24}$ alkyl group, perfluoroalkyl (meth)acrylates comprising at least one $C_{11}$-$C_{15}$ perfluoroalkyl group, N-alkyl(meth)acrylamides comprising at least one $C_{14}$-$C_{24}$ alkyl group with or without a fluorine atom, vinyl esters comprising at least one chain chosen from alkyl and perfluoro(alkyl) chains comprising at least one $C_{14}$-$C_{24}$ alkyl group (with at least 6 fluorine atoms per perfluoroalkyl chain), vinyl ethers comprising at least one chain chosen from alkyl and perfluoro(alkyl) chains comprising at least one $C_{14}$-$C_{24}$ alkyl group and at least 6 fluorine atoms per perfluoroalkyl chain, $C_{14}$ to $C_{24}$ alpha-olefins such as octadecene, para-alkylstyrenes comprising at least one $C_{12}$-$C_{24}$ alkyl group, and mixtures thereof.

When the semi-crystalline polymers result from a polycondensation, the hydrocarbon-based and/or fluorinated crystallizable chains as defined above are borne by a monomer chosen, for example, from a diacid, a diol, a diamine and a diisocyanate.

When the semi-crystalline polymers disclosed herein are copolymers, they further comprise from 0 to 50% of groups Y and Z resulting from the copolymerization:

a) of at least one Y monomer chosen from polar and non-polar monomers:
  When Y is a polar monomer, it may be chosen from a monomer comprising at least one group chosen from polyoxyalkylenated groups (such as oxyethylenated and oxypropylenated groups), a hydroxyalkyl (meth)acrylate, for instance hydroxyethyl acrylate, (meth)acrylamide, an N-alkyl(meth)acrylamide, an N,N-dialkyl (meth)acrylamide such as N,N-diisopropylacrylamide or N-vinylpyrrolidone (NVP), N-vinylcaprolactam, a monomer comprising at least one carboxylic acid group, for instance (meth)acrylic acid, crotonic acid, itaconic acid, maleic acid or fumaric acid, and a monomer comprising at least one carboxylic acid anhydride group, for instance maleic anhydride, and mixtures thereof.

When Y is a non-polar monomer, it may be chosen from an ester of the linear, branched or cyclic alkyl (meth)acrylate type, a vinyl ester, an alkyl vinyl ether, an alpha-olefin, styrene or styrene substituted with at least one $C_1$ to $C_{10}$ alkyl group, for instance α-methylstyrene, and a macromonomer of the polyorganosiloxane type comprising at least one vinyl unsaturation.

For the purposes of the disclosure, the term "alkyl" means a saturated group of, such as $C_8$ to $C_{24}$, further for example $C_{14}$ to $C_{24}$, except where otherwise mentioned; and b) of at least one Z polar monomer wherein, Z has the same definition as the "polar Y" defined above.

For instance, the semi-crystalline polymers comprising at least one crystallizable pendent chain may be chosen from alkyl (meth)acrylate and alkyl(meth)acrylamide homopolymers comprising at least one alkyl group as defined above, such as at least one $C_{14}$-$C_{24}$ alkyl group, copolymers of these monomers with at least one hydrophilic monomer, for example, of different nature from (meth)acrylic acid, for instance N-vinylpyrrolidone and hydroxyethyl (meth)acrylate, and mixtures thereof.

B) Polymers Bearing in the Skeleton at Least One Crystallizable Block

For instance, these polymers may be chosen from block copolymers comprising at least two blocks of different chemical nature, one of which is crystallizable.

For example, the block polymers defined in U.S. Pat. No. 5,156,911 may be used.

In another example, block copolymers of olefin or of cycloolefin comprising at least one crystallizable chain, for instance those derived from the block polymerization of at least one monomer chosen from:

cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, and dicyclopentadiene, with at least one monomer chosen from ethylene, propylene, 1-butene, 3-methyl-1-butene, 1-hexene, 4-methyl-1-pentene, 1-octene, 1-decene and 1-eicosene, and such as copoly(ethylene/norbornene) blocks and (ethylene/propylene/ethylidene-norbornene) block terpolymers. Those resulting from the block copolymerization of at least two $C_2$-$C_{16}$, for example, $C_2$-$C_{12}$ and further for example, $C_4$-$C_{12}$ α-olefins such as those mentioned above and yet further for example, block bipolymers of ethylene and of 1-octene may also be used.

The copolymers may be copolymers comprising at least one crystallizable block, wherein the copolymer residue is amorphous (at room temperature). These copolymers may also comprise two crystallizable blocks of different chemical nature. For example, the copolymers may be chosen, for example, from those that simultaneously comprise, at room temperature, a crystallizable block and an amorphous block that are both hydrophobic and lipophilic, sequentially distributed; non-limiting mention may be made, for example, of polymers comprising one of the crystallizable blocks and one of the amorphous blocks below:

A block that is crystallizable by nature: a) polyester, for instance poly(alkylene terephthalate), b) polyolefin, for instance polyethylenes and polypropylenes.

An amorphous and lipophilic block, for instance amorphous polyolefins and copoly(olefin)s such as poly (isobutylene), hydrogenated polybutadiene and hydrogenated poly(isoprene).

Non-limiting examples of such copolymers comprising a crystallizable block and a separate amorphous block which may be mentioned include:

a) poly(ε-caprolactone)-b-poly(butadiene) block copolymers, for example, those which are hydrogenated, such as those described in the article "Melting behavior of poly(ε-caprolactone)-block-polybutadiene copolymers" from S, Nojima, Macromolecules, 32, 3727-3734 (1999), b) the hydrogenated block and multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995), c) the poly(ethylene)-b-copoly(ethylene/propylene) block copolymers cited in the articles "Morphology of semi-crystalline block copolymers of ethylene-(ethylene-alt-propylene)" by P. Rangarajan et al., Macromolecules, 26, 4640-4645 (1993) and "Polymer aggregates with crystalline cores: the system poly(ethylene)-poly(ethylene-propylene)" by P. Richter et al., Macromolecules, 30, 1053-1068 (1997), and d) the poly(ethylene)-b-poly(ethylethylene) block copolymers cited in the general article "Crystallization in block copolymers" by I. W. Hamley, Advances in Polymer Science, Vol. 148, 113-137 (1999).

The semi-crystalline polymers in the composition of the disclosure may be partially crosslinked, provided that the degree of crosslinking does not interfere with their dissolution or dispersion in the liquid fatty phase by heating above their melting point. It may then be a chemical crosslinking, by reaction with a multifunctional monomer during the polymerization. It may also be a physical crosslinking which may, in this case, be due either to the establishment of bonds of hydrogen or dipolar type between groups borne by the polymer, such as the dipolar interactions between carboxylate ionomers, these interactions being of small amount and borne by the polymer skeleton; or to a phase separation between the crystallizable blocks and the amorphous blocks borne by the polymer.

For instance, the semi-crystalline polymers in the composition according to the disclosure are non-crosslinked.

In one embodiment, the semi-crystalline polymer may be chosen from copolymers resulting from the polymerization of at least one monomer comprising a crystallizable chain chosen from saturated $C_{14}$ to $C_{24}$ alkyl (meth)acrylates, $C_{11}$ to $C_{15}$ perfluoroalkyl (meth)acrylates, $C_{14}$ to $C_{24}$ N-alkyl(meth) acrylamides with or without a fluorine atom, vinyl esters comprising at least one chain chosen from $C_{14}$ to $C_{24}$ alkyl and perfluoroalkyl chains, vinyl ethers comprising at least one chain chosen from $C_{14}$ to $C_{24}$ alkyl and perfluoroalkyl chains, $C_{14}$ to $C_{24}$ alpha-olefins, para-alkylstyrenes with an alkyl group comprising from 12 to 24 carbon atoms; with at least one monomer chosen from optionally fluorinated $C_1$ to $C_{10}$ monocarboxylic acid esters and amides of the following formula:

wherein $R_1$ is chosen from H and $CH_3$, $R_2$ is a group chosen from optionally fluorinated $C_1$-$C_{10}$ alkyl groups and X is chosen from O, NH and $NR_3$ wherein $R_3$ is a group chosen from optionally fluorinated $C_1$-$C_{10}$ alkyl groups.

In one embodiment, the semi-crystalline polymer is derived from a monomer comprising a crystallizable chain, chosen from saturated $C_{14}$ to $C_{22}$ alkyl (meth)acrylates.

Among non-limiting examples of the structuring semi-crystalline polymers that may be used in the composition according to the disclosure, mention may be made of the products Intelimer® from the company Landec, described in the brochure "Intelimer® polymers", Landec IP22 (Rev. 4-97). These polymers are in solid form at room temperature (25° C.). They comprise crystallizable pendent chains and have the formula X above.

For example, the semi-crystalline polymers may be chosen from: those described in Examples 3, 4, 5, 7, 9 and 13 of U.S. Pat. No. 5,156,911, comprising a—COOH group, resulting from the copolymerization of acrylic acid and of $C_5$ to $C_{16}$ alkyl (meth)acrylate, and further for example, of the copolymerization:

of acrylic acid, of hexadecyl acrylate and of isodecyl acrylate in a 1/16/3 weight ratio, of acrylic acid and of pentadecyl acrylate in a 1/19 weight ratio, of acrylic acid, of hexadecyl acrylate and of ethyl acrylate in a 2.5/76.5/20 weight ratio, of acrylic acid, of hexadecyl acrylate and of methyl acrylate in a 5/85/10 weight ratio, of acrylic acid and of octadecyl methacrylate in a 2.5/97.5 weight ratio, and of hexadecyl acrylate, of polyethylene glycol methacrylate monomethyl ether comprising 8 ethylene glycol units, and of acrylic acid in an 8.5/1/0.5 weight ratio.

For instance, it may also be possible to use the structure "O" from National Starch, as described in U.S. Pat. No. 5,736,125, with a melting point of 44° C., and also semi-crystalline polymers with crystallizable pendent chains comprising fluoro groups, as described in Examples 1, 4, 6, 7 and 8 of document WO-A-01/19333.

For example, it may also be possible to use low-melting semi-crystalline polymers obtained by copolymerization of stearyl acrylate and of acrylic acid or of NVP, as described in U.S. Pat. No. 5,519,063 or document EP-A-550 745 and further for example, those described in Examples 1 and 2 below, for the preparation of polymers, with a melting point of 40° C. and 38° C., respectively.

In another example, it is also possible to use semi-crystalline polymers obtained by copolymerization of behenyl acrylate and of acrylic acid or of NVP, as described in U.S. Pat. No. 5,519,063 and document EP-A-550 745, and further for example, those described in Examples 3 and 4 below, for the preparation of polymers, with a melting point of 60° C. and 58° C., respectively.

The semi-crystalline polymer in aqueous dispersion may be present in the composition according to the disclosure in a polymer solids content (or active materials content) ranging, for example, from 1% to 40% by weight, further for example, from 5% to 30% by weight and even further for example, from 5% to 20% by weight, relative to the total weight of the composition.

For instance, the size of the particles of the at least one semi-crystalline polymer in aqueous dispersion may range from 1 µm to 50 µm, such as from 1 µm to 25 µm.

Fillers

The solid particles present in the composition according to the disclosure may comprise at least one filler.

The term "filler" means any colourless or white particle chosen from mineral and organic, lamellar, spherical and oblong fillers, which are chemically inert in the composition.

For example, the fillers may be chosen from those that are well known to a person skilled in the art and that are commonly used in cosmetic compositions. The fillers may be mineral and organic, and lamellar and spherical. Non-limiting mention may be made of talc, mica, silica, kaolin, polyamide powders, for instance Nylon® (Orgasol from Atochem), poly-β-alanine powders and polyethylene powders, tetrafluoroethylene polymer powders, for instance Teflon®, lauroyl lysine, starch, boron nitride, hollow polymer microspheres such as those of polyvinylidene chloride/acrylonitrile, for instance Expancel®(Nobel Industrie), acrylic powders such as Polytrap® (Dow Corning), polymethyl methacrylate particles and silicone resin microbeads (for example Tospearls® from Toshiba), precipitated calcium carbonate, magnesium carbonate, magnesium hydrocarbonate, hydroxyapatite, hollow silica microspheres (Silica Beads® from Maprecos), glass or ceramic microcapsules, metal soaps derived from carboxylic organic acids comprising from 8 to 22 carbon atoms, such as from 12 to 18 carbon atoms, for example zinc stearate, magnesium stearate, lithium stearate, zinc laurate and magnesium myristate, and mixtures thereof.

For instance, the at least one filler may be present in an amount ranging from 0.1% to 25%, for example, from 1% to 20% by weight of the total weight of the composition.

In one example, the at least one filler used in the composition according to the disclosure may have a mean size ranging from 0.1 to 30 µm.

Pigments

The solid particles present in the composition according to the disclosure may be chosen from pigments.

The term "pigments" means white or coloured, mineral or organic particles, which are insoluble in the physiologically acceptable aqueous medium of the composition, intended to colour and/or opacify the composition. Pigments may also comprise nacres or nacreous pigments, which are iridescent particles, produced, for example, by certain molluscs in their shell, or alternatively synthesized.

Among the mineral pigments, non-limiting mention may be made of titanium dioxide, optionally surface-treated, zirconium oxide or cerium oxide, and also iron oxide or chromium oxide, manganese violet, ultramarine blue, chromium hydrate and ferric blue, and the mixtures thereof. Among the organic pigments, non-limiting mention may be made of carbon black, pigments of D & C type, and lakes based on cochineal carmine or on barium, strontium, calcium or aluminium, and mixtures thereof. Pigments treated with at least one hydrophobic agent may also be used. The at least one hydrophobic treating agent may be chosen from silicones, for instance methicones, dimethicones and perfluoroalkylsilanes; fatty acids, for instance stearic acid; metal soaps, for instance aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkylperfluoropolyether groups, and amino acids; N-acyl amino acids and salts thereof; lecithin, and isopropyl triisostearyl titanate, and mixtures thereof. The N-acyl amino acids may comprise an acyl group comprising from 8 to 22 carbon atoms, for instance a 2-ethylhexanoyl, caproyl, lauroyl, myristoyl, palmitoyl, stearoyl, or cocoyl group. The salts thereof may be chosen from aluminium, magnesium, calcium, zirconium, zinc, sodium and potassium salts. The amino acid may be chosen, for example, from lysine, glutamic acid and alanine.

The term "alkyl" mentioned in the at least one hydrophobic treating agent mentioned above is an alkyl group comprising, for example, from 1 to 30 carbon atoms, further for example, from 5 to 16 carbon atoms.

For example, hydrophobic-treated pigments are described in document EP-A-1 086 683.

It is also possible to use pigments with certain optical effect, for instance glass particles coated with at least one metal, such as gold, silver and platinum.

The nacres or nacreous pigments are iridescent particles, produced, for example, by certain molluscs in their shell, or alternatively synthesized, which are insoluble in the physiologically acceptable medium of the composition. They may be chosen from white nacreous pigments such as mica coated with titanium or with bismuth oxychloride, coloured nacreous pigments such as titanium mica with iron oxides, titanium mica with, for example, ferric blue or with chromium oxide, titanium mica with an organic pigment of the above-mentioned type and also nacreous pigments based on bismuth oxychloride, and mixtures thereof. Interference pigments, such as those comprising liquid crystals or multilayers, may also be used.

For instance; the pigments may be present in an amount ranging from 0.01% to 25%, for example, from 0.1% to 20% and further for example, from 1% to 10% by weight of the total weight of the composition.

Rheological Agent

The second solid particles may also comprise at least one rheological agent.

For example, this at least one rheological agent is chosen from lipophilic gelling agents.

The lipophilic gelling agent may be organic or mineral, and polymeric or molecular.

Mineral lipophilic gelling agents that non-limiting mention may be made of include optionally modified clays, for instance hectorites modified with a $C_{10}$ to $C_{22}$ fatty acid ammonium chloride, for instance hectorite modified with distearyldimethylammonium chloride.

The polymeric organic lipophilic gelling agents are chosen, for example, from partially and totally crosslinked elastomeric organopolysiloxanes of three-dimensional structure, for instance those sold under the names KSG6, KSG16 and KSG18 from Shin-Etsu, Trefil E-505C or Trefil E-506C from Dow Corning, Gransil SR-CYC, SR DMF10, SR-DC556, SR 5CYC gel, SR DMF 10 gel and SR DC 556 gel from Grant Industries, and SF 1204 and JK 113 from General Electric; ethylcelluloses, for instance those sold under the name Ethocel by Dow Chemical; polyamides, such as copolymers of a $C_{36}$ diacid condensed with ethylenediamine, with a weight-average molecular mass of about 6000, such as those sold by the company Arizona Chemical under the names Uniclear 80 and Uniclear 100; gums, for example silicone gums, such as PDMS having a viscosity>100,000 centiskokes and galactomannans comprising from 1 to 6 and for example, from 2 to 4 hydroxyl groups per saccharide, substituted with at least one alkyl chain chosen from saturated and unsaturated alkyl chains, for instance guar gum alkylated with at least one alkyl chain chosen from $C_1$ to $C_6$ and for example, $C_1$ to $C_3$ alkyl chains, and mixtures thereof.

For example, the lipophilic gelling agents that may be used include non-polymeric, molecular organic gelling agents, also known as organogelling agents, combined with a liquid fatty phase, which may be chosen from those whose molecules are capable of establishing between themselves physical interactions leading to self-aggregation of the molecules with formation of a supramolecular 3D network that is responsible for the gelation of the liquid fatty phase.

As disclosed herein, the term "liquid fatty phase" means a fatty phase that is liquid at room temperature (25° C.) and atmospheric pressure (760 mmHg, i.e. 105 Pa), comprising at least one fatty substance that is liquid at room temperature, also known as oils, which are generally mutually compatible.

For instance, the oils may be chosen from any physiologically acceptable oils, such as cosmetically acceptable oils, for example, mineral, animal, plant or synthetic oils; further for example, oils chosen from volatile and non-volatile, hydrocarbon-based oils, silicone oils, and fluoro oils, and mixtures thereof. The term "hydrocarbon-based oil" means an oil mainly comprising carbon and hydrogen atoms and possibly at least one functional group chosen from hydroxyl, ester, ether and carboxylic functional groups. For example, the oils may have a viscosity ranging from 0.5 to 100 000 cps, further for example, from 50 to 50 000 cps, and even further for example, from 100 to 300 000 cps.

Among non-limiting examples of oils that may be used, mention may be made of:

hydrocarbon-based oils of animal origin, such as perhydrosqualene;

hydrocarbon-based plant oils such as liquid triglycerides of fatty acids of from 4 to 24 carbon atoms, for instance heptanoic or octanoic acid triglyceride, or alternatively sunflower oil, maize oil, soybean oil, marrow oil, grapeseed oil, sesame seed oil, hazelnut oil, apricot oil, macadamia oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter;

linear and branched hydrocarbons of mineral or synthetic origin, for example, liquid paraffin and derivatives thereof, petroleum jelly, polydecenes, polybutenes and hydrogenated polyisobutene, for example parleam;

synthetic esters and ethers, such as those of fatty acids, for instance the oils of formula $R_4COOR_5$ wherein $R_4$ is chosen from higher fatty acid residues comprising from 1 to 40 carbon atoms and $R_5$ is chosen from hydrocarbon-based chains comprising from 1 to 40 carbon atoms with the number of carbon atoms in $(R_4+R_5) \leq 10$, for instance purcellin oil, isononyl isononanoate, isopropyl myristate, 2-ethylhexyl palmitate, 2-octyldodecyl stearate, 2-octyldodecyl erucate, isostearyl isostearate and tridecyl trimellitate; hydroxylated esters, for instance isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

fatty alcohols comprising from 12 to 26 carbon atoms, for instance octyldodecanol, 2-butyloctanol, 2-hexyldecanol, 2-undecylpentadecanol and oleyl alcohol;

fluoro oils chosen from optionally partially hydrocarbon-based and silicone-based fluoro oils;

silicone oils, chosen, for example, from volatile and non-volatile, linear and cyclic polydimethylsiloxanes (PDMSs); polydimethylsiloxanes comprising at least one group chosen from alkyl, alkoxy and phenyl groups, which is pendent or at the end of a silicone chain, wherein the at least one group comprises from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenyl ethyl trimethyl siloxysilicates, and mixtures thereof.

The supramolecular network may result from the formation of a network of fibrils (caused by the stacking or aggregation of organogelling molecules), which may immobilize the molecules of the liquid fatty phase.

The ability to form this network of fibrils, and thus to gel, may depend on at least one property chosen from the nature (or chemical class) of the organogelling agent, the nature of the substituents borne by its molecules for a given chemical class, and the nature of the liquid fatty phase.

The physical interactions are of diverse nature but exclude co-crystallization. For example, these physical interactions may be interactions of self-complementary hydrogen interaction type, π interactions between unsaturated rings, dipolar interactions, coordination bonds with organometallic derivatives, and combinations thereof. For instance, each molecule of an organogelling agent can establish several types of physical interaction with a neighbouring molecule. In one aspect, the molecules of the organogelling agents according to the disclosure comprise at least one group capable of establishing hydrogen bonds, for example at least two groups capable of establishing hydrogen bonds, at least one aromatic ring, for example at least two aromatic rings, at least one ethylenically unsaturated bond, and/or at least one asymmetric carbon. In one example, the groups capable of forming hydrogen bonds may be chosen from hydroxyl, carbonyl, amine, carboxylic acid, amide, urea and benzyl groups, and combinations thereof.

The organogelling agents according to the disclosure may be soluble in the liquid fatty phase after heating to obtain a transparent uniform liquid phase. They may also be solid or liquid at room temperature and atmospheric pressure.

Examples of molecular oranogelling agents that may be used in the composition according to the disclosure include those described in the document "Specialist Surfactants" edited by D. Robb, 1997, pp. 209-263, Chapter 8 by P. Terech, documents EP-A-1 068 854 and EP-A-1 086 945, or alternatively in document WO-A-02/47031.

Non-limiting mention may be made, among these organogelling agents, of amides of carboxylic acids, for example amides of tricarboxylic acids, such as cyclohexanetricarboxamides (see document EP-A-1 068 854), diamides with hydrocarbon-based chains each comprising from 1 to 22 carbon atoms, for example from 6 to 18 carbon atoms, wherein the hydrocarbon-based chains may be unsubstituted or substituted with at least one substituent chosen from ester, urea and fluoro groups (see document EP-A-1 086 945) and further for example diamides resulting from the reaction of diaminocyclohexane, such as diaminocyclohexane in trans form, and of an acid chloride, for instance N,N'-bis(dodecanoyl)-1,2-diaminocyclohexane, N-acylamino acid amides, for instance the diamides resulting from the action of an N-acylamino acid with amines comprising from 1 to 22 carbon atoms, for instance those described in document WO-93/23008 such as N-acylglutamic acid amides in which the acyl group is a $C_8$ to $C_{22}$ alkyl chain, such as N-lauroyl-L-glutamic acid dibutylamide, manufactured or sold by the company Ajinomoto under the name GP-1, and mixtures thereof.

The compositions may comprise from 0.05% to 10% by weight of the at least one rheological agent, relative to the total weight of the composition. For example, the compositions may comprise from 0.1% to 5% by weight, and further for example from 0.5% to 3% by weight, of the at least one rheological agent, relative to the total weight of the composition.

Other Ingredients

The composition according to the disclosure may further comprise fibres to allow an improvement in the lengthening effect.

The term "fibre" means an object of length L and diameter D such that L is very much greater than D, wherein D is the diameter of the circle in which the cross section of the fibre is inscribed. For instance, the ratio L/D (or shape factor) is chosen in the range from 3.5:1 to 2 500:1, for example from 5:1 to 500:1, and further for example from 5:1 to 150:1.

The fibres that may be used in the composition of the disclosure may be chosen from mineral and organic fibres of synthetic or natural origin. For example, they may be short or long, individual or organized, such as being braided, and hollow or solid. They may have any shape, such as a circular or polygonal (square, hexagonal or octagonal) cross section, depending on the intended specific application. For example, their ends may be blunt and/or polished to prevent injury.

For instance, the fibres may have a length ranging from 1 μm to 10 mm, for example from 0.1 mm to 5 mm, and further for example from 1 mm to 3.5 mm. Their cross sections may, for example, be a circle of diameter ranging from 2 nm to 500 μm, further for example from 100 nm to 100 μm, and even further for example from 1 μm to 50 μm. The weight or yarn count of the fibres may be given in units of denier or decitex, and may represent the weight in grams per 9 km of yarn. In one embodiment, the fibres according to the disclosure may have a yarn count chosen in the range from 0.15 to 30 denier, for example from 0.18 to 18 denier.

The fibres can be those used in the manufacture of textiles, for example, silk fibre, cotton fibre, wool fibre, flax fibre, cellulose fibre extracted, for example, from wood, from plants or from algae, rayon fibre, polyamide (Nylon®) fibre, viscose fibre, acetate fibre, such as rayon acetate fibre, poly (p-phenyleneterephthalamide) (or aramide) fibre, such as Kevlar® fibre, acrylic polymer fibre, such as polymethyl methacrylate fibre and poly(2-hydroxyethyl methacrylate) fibre, polyolefin fibre, such as polyethylene fibre and polypropylene fibre, glass fibre, silica fibre, carbon fibre, such as in graphite form, polytetrafluoroethylene (such as Teflon®) fibre, insoluble collagen fibre, polyester fibre, polyvinyl chloride fibre and polyvinylidene chloride fibre, polyvinyl alcohol fibre, polyacrylonitrile fibre, chitosan fibre, polyurethane fibre, polyethylene phthalate fibre, and fibres formed from a mixture of polymers such as those mentioned above, for instance polyamide/polyester fibres.

The fibres used in surgery may also be used, for instance the resorbable synthetic fibres prepared from glycolic acid and caprolactone (Monocryl from Johnson & Johnson); resorbable synthetic fibres of the type which is a copolymer of lactic acid and of glycolic acid (Vicryl from Johnson & Johnson); polyterephthalic ester fibres (Ethibond from Johnson & Johnson) and stainless steel threads (Acier from Johnson & Johnson).

Moreover, the fibres may be treated or untreated at the surface, and coated or uncoated. As coated fibres that may be used, non-limiting mention may be made of polyamide fibres coated with copper sulphide, which may provide an antistatic effect (for example R-STAT from Rhodia), or another polymer which may enable a particular organization of the fibres (specific surface treatment), or surface treatment, such as colour/hologram effects (Lurex fibre from Sildorex, for example).

For example, fibres of synthetic origin for instance organic fibres, such as those used in surgery, may be used. Further for example, water-insoluble fibres may be used.

The fibres that may be used in the composition according to the disclosure may, for example, be chosen from polyamide fibres, cellulose fibres, poly(p-phenyleneterephthalamide) fibres, and polyethylene fibres. Their length (L) may range from 0.1 mm to 5 mm, for example from 0.25 mm to 1.6 mm, and their mean diameter may range from 1 μm to 50 μm. For instance, the polyamide fibres sold by Etablissements P. Bonte under the name "Polyamide 0.9 Dtex 3 mm", having a mean diameter of 6 μm, a yarn count of about 0.9 dtex and a length ranging from 0.3 mm to 5 mm, may be used. Cellulose (or rayon) fibres with a mean diameter of 50 μm and a length ranging from 0.5 mm to 6 mm may also be used, for instance those sold under the name "Natural rayon flock fiber RC1 BE-N003-M04" by the company Claremont Flock. Polyethylene fibres, for instance those sold under the name "Shurt Stuff 13 099 F" by the company Mini Fibers, may also be used.

The composition according to the disclosure may also comprise "rigid" fibres, as opposed to the fibres mentioned above, which may not be rigid fibres.

The rigid fibres, which are initially substantially straight, when placed in a dispersing medium, do not undergo a substantial change in shape, which is reflected by the angular condition defined below, reflecting a shape that may be described as still substantially straight and linear. This angle condition reflects the stiffness of the fibres, which may be difficult to express by another parameter for objects that are as small as the rigid fibres.

The stiffness of the fibres is reflected by the following angular condition: for example, at least 50%, further for example at least 75%, and in yet another example at least 90%, in numerical terms, of the fibres are such that the angle formed between the tangent to the longitudinal central axis of the fibre and the straight line connecting the end to the point on the longitudinal central axis of the fibre corresponding to half the length of the fibre is less than 15°, and the angle formed between the tangent to the longitudinal central axis of the fibre at a point half way along the fibre and the straight line connecting one of the ends to the point on the longitudinal central axis of the fibre corresponding to half the length of the fibre, is less than or equal to 15° for the same fibre length ranging from 0.8 mm to 5 mm, for example from 1 mm to 4 mm, further for example from 1 mm to 3 mm, and even further for example being 2 mm.

For instance, the angle mentioned above is measured at the two ends of the fibre and at a point half way along the fibre; i.e., three measurements are taken and the average of the measured angles is less than or equal to 15°.

For example, the tangent, at any point on the fibre, may form an angle of less than 15°.

As disclosed herein, the angle formed by the tangent at a point on the fibre is the angle formed between the tangent to the longitudinal central axis of the fibre at the point on the fibre and, the straight line connecting the end of the fibre that is closest to the point to the point on the longitudinal central axis of the fibre corresponding to half the length of the fibre.

In one aspect, the rigid fibres that may be used in the composition according to the disclosure have the same or substantially the same fibre length.

For instance, when a medium in which the rigid fibres are dispersed to a fibre concentration of 1% by weight is observed by microscope, with an objective lens allowing a magnification of 2.5 and with full-field vision, a numerical majority of the rigid fibres, i.e. at least 50% numerically of the rigid fibres, for example at least 75% numerically of the rigid fibres, and further for example at least 90% numerically of the rigid fibres, should satisfy the angular condition defined above. The measurement leading to the angle value is performed for the same length of fibres, wherein this length is in the range from 0.8 mm to 5 mm, for example from 1 to 4 mm, and further for example from 1 to 3 mm, and even further for example is 2 mm.

The medium in which the observation is performed is a dispersing medium that can ensure good dispersion of the rigid fibres, for example water or an aqueous gel of clay or of associative polyurethane. A direct observation of the composition comprising the rigid fibres may even be performed. A sample of the prepared composition or dispersion is placed between a slide and cover slip for observation by microscope with an objective lens allowing a magnification of 2.5 and with full-field vision. Full-field vision can allow the fibres to be viewed in their entirety.

The rigid fibres may be chosen from fibres of a synthetic polymer chosen from polyesters, polyurethanes, acrylic polymers, polyolefins, polyamides, such as non-aromatic polyamides, and aromatic polyimideamides.

Non-limiting examples of rigid fibres that may be mentioned include:
- polyester fibres, such as those obtained by chopping yarns sold under the names Fibre 255-100-R11-242T Taille 3 mm (eight-lobed cross section), Fibre 265-34-R11-56T Taille 3 mm (round cross section) and Fibre Coolmax 50-34-591 Taille 3 mm (four-lobed cross section) by the company Dupont de Nemours;
- polyamide fibres, such as those sold under the names Tri-lobal Nylon 0.120-1.8 DPF; Trilobal Nylon 0.120-18 DPF; Nylon 0.120-6 DPF by the company Cellusuede Products; or obtained by chopping yarns sold under the name Fibre Nomex Brand 430 Taille 3 mm by the company Dupont de Nemours;
- polyimideamide fibres, such as those sold under the names "Kermel" and "Kermel Tech" by the company RHODIA;
- poly(p-phenyleneterephthalamide) (or aramide) sold, for example under the name Kevlar® by the company Dupont de Nemours;
- fibres with a multilayer structure comprising alternating layers of polymers chosen from polyesters, acrylic polymers and polyamides, such as those described in documents EP-A-6 921 217, EP-A-686 858 and U.S. Pat. No. 5,472,798. Such fibres are, for example, sold under the names "Morphotex" and "Teijin Tetron Morphotex" by the company Teijin.

For example, the rigid fibres may be chosen from aromatic polyimideamide fibres. Further for example, polyimideamide yarns or fibres that may be used for the compositions of the disclosure are described, for example, in the document from R. Pigeon and P. Allard, "Hitzebeständige and flammfeste Fasern," Die Angewandte Makromolekulare Chemie, Band 40/41 (1974), pages 139-158 (No. 600), or in U.S. Pat. No. 3,802,841, or in documents FR-A-2 079 785, EP-A1-0 360 728 and EP-A-0 549 494.

Further for example, the aromatic polyimideamide fibres may be chosen from polyimideamide fibres comprising repeating units of formula:

that may be obtained by polycondensation of tolylene diisocyanate and trimellitic anhydride.

The fibres may be present in the composition according to the disclosure in an amount ranging from 0.01% to 10% by weight, for example from 0.1% to 5% by weight, and further for example from 0.3% to 3% by weight relative to the total weight of the composition.

The composition according to the disclosure may further comprise at least one additional ingredient chosen from those usually used in cosmetics. Such at least one additional ingredient may be chosen from plasticizers, coalescers, liposoluble and water-soluble dyes, surfactants, preserving agents, oils, moisturizers, and fragrances, which are well known in the fields under consideration.

Needless to say, persons of ordinary skill in the art will take care to select this (these) ingredient(s) and/or the amount thereof such that at least one beneficial property of the composition according to the disclosure is not, or is not substantially, adversely affected by the envisaged addition.

The compositions according to the disclosure may also comprise at least one adjuvant chosen from the common adjuvants such as basifying or acidifying agents, texture agents, spreading additives, plasticizers and water-soluble active ingredients commonly used in cosmetic preparations for keratin fibres.

The composition according to the disclosure may be prepared according to the usual methods in the fields under consideration.

The examples that follow illustrate the present disclosure in a non-limiting manner.

The amounts indicated are percentages by weight and are expressed relative to the total weight of the composition, unless otherwise specified.

The rheological measurements were performed using a Haake RS 75 controlled-stress rheometer under the following conditions:
measuring temperature: 25° C.
stress sweep from 1 to 2000 Pa
measuring frequency: 1 Hz.

EXAMPLE 1

Preparation of a Microdispersion of Beeswax

A microdispersion of beeswax having the composition below was prepared:

| | |
|---|---|
| Beeswax | 40% |
| Sodium stearate | 4% |
| Preserving agent | 0.4% |
| Water | qs 100 |

Procedure

The wax, the sodium stearate and the preserving agent were heated to a temperature of 75-80° C. and dispersed coarsely for 2 minutes in a tank with stirring (paddles and turbomixer) at 1500 rpm. The mixture was then high-pressure homogenized several times, while the temperature was kept at 75-80° C., until the pressure stabilized (pressure 1st stage: 700 bar, 2nd stage: 320 bar).

The mixture was cooled to room temperature (plate cooler).

The wax particles of this microdispersion had a size of 134 nm.

EXAMPLE 2

Mascara Composition

A mascara having the composition below was prepared:

| | |
|---|---|
| Oxyethylenated (100 EO) stearyl alcohol/ polyethylene glycol (136 EO) hexamethylene diisocyanate copolymer** (SER AD FX 1100 from the company Servo Delden) | 2% |
| Aqueous dispersion of aliphatic polyurethane containing 38% active material (Avalure UR-450 from the company Noveon-Goodrich), particle size: about 66 nm) | 8% (a.m.)* |
| Wax microdispersion of Example 1 | 10% (a.m.) |
| Beeswax | 10% |
| Black iron oxide | 5% |
| Propylene glycol | 5% |
| Polytetrafluoroethylene powder (Teflon ®) | 5% |
| Ethanol | 5% |
| Preserving agents (propyl paraben/ methyl paraben) | qs |
| Water | qs 100 |

*a.m. = active material
**associative polymer
Size of the beeswax particles: about 5–10 μm
Size of the filler particles (polytetrafluoroethylene powder): about 8–13 μm Procedure The associative polymer (SER AD FX 1100) was dispersed in the water at 40° C. so as to obtain a gel, and the mixture was then allowed to return to room temperature with stirring.

The latex (Avalure UR-450) was then added, with continued stirring, followed by addition of the black iron oxide, which was predispersed in the propylene glycol and grounded in the three-roll mill.

The mixture was stirred for 15 minutes (the state of dispersion of the pigment was checked by microscope) and the temperature was than raised to 70° C.

In parallel, the wax and the preserving agent were melted at a temperature of about 100° C. and this waxy phase was then added to the mixture. The resulting mixture was stirred for 15 minutes and then cooled gradually to room temperature.

The wax microdispersion of Example 1, the preserving agent diluted in the alcohol and then the polytetrafluoroethylene powder were subsequently added.

This mascara had a threading nature of 16.7 mm and an elasticity 5 equal to 36°, and presented continuous and uniform flow.

This mascara was judged as having a fluid, shiny texture, and made it possible to obtain on the eyelashes, after application, a smooth, uniform film and also satisfactory lengthening of the eyelashes.

EXAMPLE 3

Mascara Composition

A mascara having the composition below was prepared:

| | |
|---|---|
| Oxyethylenated (100 EO) stearyl alcohol/ polyethylene glycol (136 EO) hexamethylene diisocyanate copolymer (SER AD FX 1100 from the company Servo Delden) | 2% |
| Aqueous dispersion of acrylic and styrene/ acrylic copolymers, containing 40% active material (Syntran 5760 from the company Interpolymer), particle size: about 48 nm | 12% (a.m.)* |
| Wax microdispersion of Example 1 | 10% (a.m.) |
| Beeswax | 6% |
| Black iron oxide | 5% |
| Propylene glycol | 5% |
| Ethanol | 5% |
| Preserving agents (propyl paraben/ methyl paraben) | qs |
| Water | qs 100 |

*a.m. = active material

The same procedure as in the above example was used.

This mascara had a threading nature of 12 mm and an elasticity 5 equal to 42°; it showed continuous and uniform flow.

When applied to the eyelashes, this mascara composition formed a uniform film, without blobs, and allowed good separation and lengthening "eyelash by eyelash".

EXAMPLE 4

Mascara Composition

A mascara having the composition below was prepared:

| | |
|---|---|
| Oxyethylenated (100 EO) stearyl alcohol/ polyethylene glycol (136 EO) hexamethylene diisocyanate copolymer (SER AD FX 1100 from the company Servo Delden) | 1.5% |
| Aqueous dispersion of aliphatic polyurethane containing 38% active material (Avalure UR-450 from the company Noveon-Goodrich, particle size: about 66 nm) | 6% (a.m.)* |
| Wax microdispersion of Example 1 | 10% (a.m.) |
| Beeswax | 11% |
| Black iron oxide | 5% |
| Propylene glycol | 5% |
| Ethylenediamine/stearyl dilinoleate dimer copolymer (Uniclear 100 VG from the company Arizona Chemical) | 0.75% |
| Polytetrafluoroethylene powder (Teflon ®) | 7% |
| Ethanol + preserving agents (propyl paraben/methyl paraben) | qs |
| Water | qs 100 |

*a.m. = active material

Procedure

The associative polymer (SER AD FX 1100) was dispersed in the water at 40° C. so as to obtain a gel, and the mixture was then allowed to return to room temperature with stirring.

The latex (Avalure UR-450) was then added, with continued stirring, followed by addition of the black iron oxide, which was predispersed in the propylene glycol and grounded in the three-roll mill.

The mixture was stirred for 15 minutes (the state of dispersion of the pigment is checked by microscope) and the temperature was than raised to 70° C.

In parallel, the wax, the Uniclear 100 VG and the preserving agent were melted at a temperature of about 100° C. and this waxy phase was then added to the mixture. The resulting mixture was stirred for 15 minutes and then cooled gradually to room temperature. The wax microdispersion of Example 1, the preserving agent diluted in the alcohol, and then, the polytetrafluoroethylene powder were subsequently added.

Figure 1:
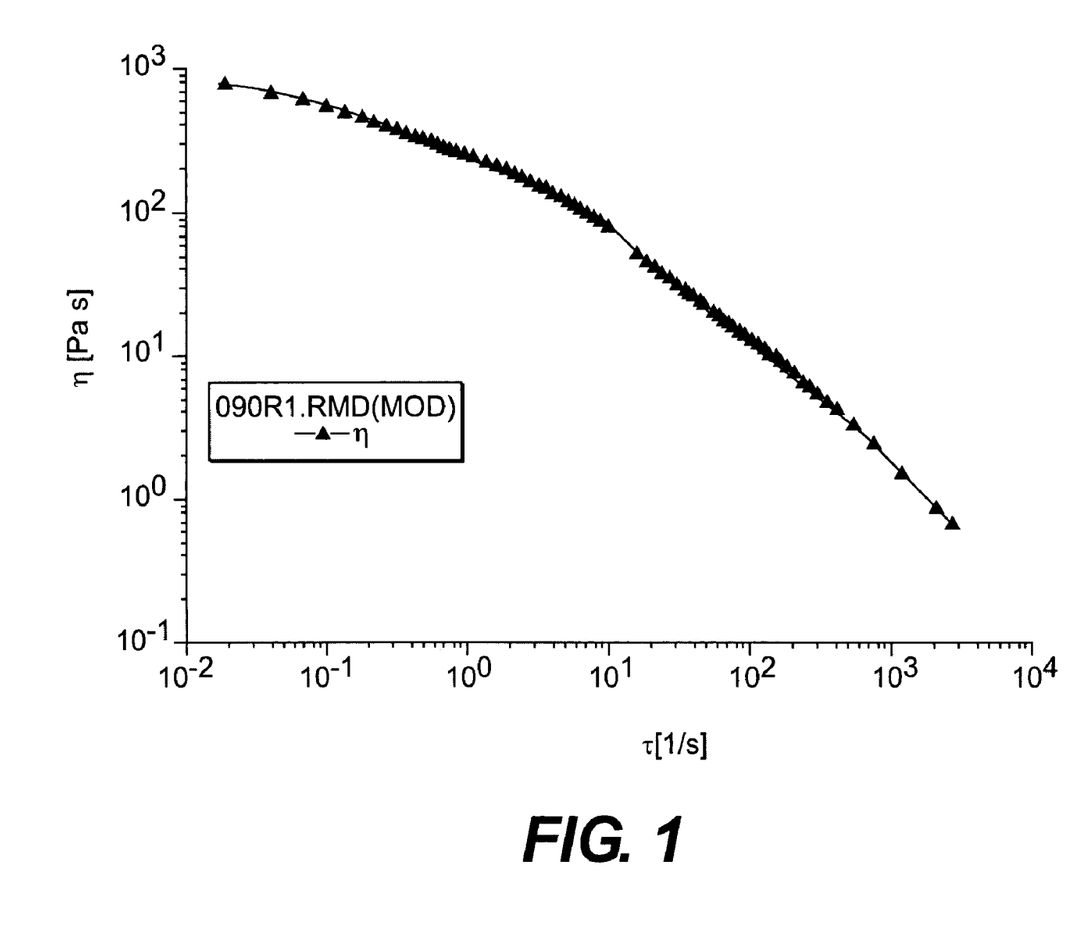

This mascara had a threading nature of 30 mm, an elasticity δ equal to 54° and continuous and uniform flow as shown by the attached FIG. 1.

For this example, $$\frac{\Delta \dot{\gamma}}{\Delta \tau}$$

ranged from $7.9 \times 10^{-3}$ to 6.88 within the shear range from $1 \times 10^{-2}$ s$^{-1}$ to $1 \times 10^{3}$ s$^{-1}$.

The mascara of this example was capable of withstanding high shears of the order of 1000 s$^{-1}$.

This figure illustrates the flow profile of the composition, showing the viscosity ($\eta$ in Pa·s) of the composition as, a function of the shear rate $\dot{\gamma}$ (in s$^{-1}$).

It confirmed that the flow was continuous and uniform, the points being equidistant on the curve.

This mascara was judged as giving, after application to the eyelashes, a smooth and uniform film of composition and also entirely satisfactory lengthening and separation of the eyelashes.

What is claimed is:

1. A cosmetic composition for coating keratin fibres, comprising, in a physiologically acceptable aqueous medium, at least one thickener, and at least one aqueous dispersion of first solid wax particles having a mean size of less than or equal to 700 nm, wherein the first solid wax particles are present in an amount ranging from 1% to 40% by weight, relative to the total weight of the composition and wherein the composition has a threading nature dmax ranging from 12 to 35 mm
wherein the at least one thickener is present in an amount ranging from 0.05% to 20% by weight of solids relative to the total weight of the composition and chosen from associative polyurethanes wherein the associative polyurethanes are chosen from triblock copolymers comprising at least one polyoxyethylenated chain comprising from 50 to 1000 oxyethylene groups.

2. The cosmetic composition according to claim 1, wherein the waxes are chosen from at least one of beeswax, Lanolin wax, Chinese insect waxes; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis, waxy copolymers and esters thereof, the waxes obtained by catalytic hydrogenation of animal or plant oils comprising at least one fatty chain chosen from linear and branched $C_3$-$C_{32}$ fatty chains, silicone waxes, and fluoro waxes.

3. The cosmetic composition according to claim 1, wherein the composition further comprises second solid particles with a mean size of greater than or equal to 701 nm.

4. The cosmetic composition according to claim 3, wherein the second solid particles are chosen from at least one of waxes, pigments, fillers, and semi-crystalline polymers.

5. The cosmetic composition according to claim 4, wherein the waxes are chosen from at least one of beeswax, Lanolin wax, Chinese insect waxes; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis, waxy copolymers and esters thereof, the waxes obtained by catalytic hydrogenation of animal or plant oils comprising at least one fatty chain chosen from linear and branched $C_8$-$C_{32}$ fatty chains, silicone waxes and fluoro waxes.

6. The cosmetic composition according to claim 4, wherein the fillers are chosen from at least one of talc, mica, silica, kaolin, polyamide powder, poly-β-alanine powder and polyethylene powder, tetrafluoroethylene polymer powders, lauroyllysine, starch, boron nitride, hollow polymer microspheres, acrylic powders, polymethyl methacrylate particles and silicone resin microbeads, precipitated calcium carbonate, magnesium carbonate, magnesium hydrocarbonate, hydroxyapatite, hollow silica microspheres, glass and ceramic microcapsules, and metal soaps derived from carboxylic organic acids comprising from 8 to 22 carbon atoms.

7. The cosmetic composition according to claim 4, wherein the semi-crystalline polymers are chosen from at least one of:
   block copolymers of polyolefins with controlled crystallization,
   polycondensates chosen from those of aliphatic and aromatic polyester types and aliphatic/aromatic copolyester types,
   homopolymers and copolymers bearing at least one crystallizable pendent chain and homopolymers and copolymers bearing at least one crystallizable block in the skeleton, and
   homopolymers and copolymers bearing at least one crystallizable pendent chain comprising at least one fluoro group.

8. The cosmetic composition according to claim 3, wherein the second particles further comprise at least one rheological agent chosen from lipophilic gelling agents.

9. The cosmetic composition according to claim 8, wherein the lipophilic gelling agents are chosen from copolymers of a $C_{36}$ diacid condensed with ethylenediamine, with a weight-average molecular mass of about 6000.

10. The cosmetic composition according to claim 1, wherein the first solid wax particles are present in an amount ranging from 5% to 30% by weight, relative to the total weight of the composition.

11. The cosmetic composition according to claim 3, wherein the second particles are present in an amount ranging from 10% to 40% by weight, relative to the total weight of the composition.

12. The cosmetic composition according to claim 1, wherein the composition has a plateau elasticity $\delta_p$ of greater than or equal to 36°.

13. The cosmetic composition according to claim 1, wherein the composition has a rheological profile such that, for a shear rate range ranging from $10^{-2}$ to $10^3$ s$^{-1}$, the ratios of the variation in the shear rates to the variation in the applied shear stresses (noted as $\frac{\Delta \dot{\gamma}}{\Delta \tau}$)

are not more than 7, wherein said composition is capable of undergoing shear stresses without fracturing throughout said shear rate range.

14. A cosmetic method for treatment or making-up keratin fibres, comprising applying to said keratin fibres a cosmetic composition according to claim 1.

15. A method for obtaining at least one result chosen from smooth and uniform film deposited on keratin fibres, a lengthening effect, and a separating effect, comprising applying to the keratin fibres, a cosmetic composition according to claim 1.

* * * * *